(12) United States Patent
Taylor

(10) Patent No.: US 7,063,863 B2
(45) Date of Patent: ***Jun. 20, 2006

(54) METHOD OF MAKING A REVERSIBLE MATRIX DRUG DELIVERY SYSTEM

(75) Inventor: Margaret Joan Taylor, Nr Loughborough (GB)

(73) Assignee: De Montfort University, Leicester (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/124,694

(22) Filed: Jul. 29, 1998

(65) Prior Publication Data

US 2002/0168409 A1    Nov. 14, 2002

Related U.S. Application Data

(63) Continuation of application No. 08/256,283, filed as application No. PCT/GB93/00034 on Jan. 8, 1993, now Pat. No. 5,830,506.

(51) Int. Cl.
*A61K 9/50* (2006.01)
(52) U.S. Cl. .................. 424/488; 424/484; 424/485
(58) Field of Classification Search ......... 424/484–486
See application file for complete search history.

(56) References Cited

U.S. PATENT DOCUMENTS 5,830,506 A    11/1998  Taylor .................. 424/488
5,902,607 A *  5/1999   Taylor .................. 424/488
6,410,053 B1 * 6/2002   Taylor .................. 424/488

OTHER PUBLICATIONS

Brownlee et al., Medline Abstr., #84029525, 1984.*

* cited by examiner

*Primary Examiner*—Michael Hartley
*Assistant Examiner*—Micah-Paul Young
(74) *Attorney, Agent, or Firm*—Renner, Otto, Boisselle & Sklar, LLP

(57) ABSTRACT

A method for producing a drug system which is a reversible gelled matrix with entrapped drug. The gel is made by combining a polysaccharide, such as dextran, a polymer of glucose, with a natural macromolecule, such as the lectin, concanavalin A, with binding sites for monomers of the polysaccharide. The drug is released in response to exposure of the matrix to free carbohydrate containing the monomer of the polysaccharide for which the natural macromolecule binds.

39 Claims, 4 Drawing Sheets

METHOD OF MAKING A REVERSIBLE MATRIX DRUG DELIVERY SYSTEM

This application is a continuation of U.S. Ser. No. 08/256,283, filed on Aug. 11, 1994 (now U.S. Pat. No. 5,830,506), which is the national phase application of PCT Application Number PCT/GB93/00034 filed Jan. 8, 1993.

This invention concerns a method for producing a drug system for delivering a drug or other agent for the treatment of a condition in a controlled release manner.

Most known 'controlled-release' drug systems are constant slow-release mechanisms (U.S. Pat. No. 4,145,410). These systems do not react to any inherent substances in the body to release the drug appropriately in response to that substance, ie. there is no feedback mechanism. Feedback mechanisms have been suggested to be of interest in vivo to maintain general homeostasis.

U.S. Pat. No. 4,348,387 discloses a feedback controlled insulin delivery system wherein glucose-insulin conjugates are displaced from glucose binding sites on a binding molecule by free glucose. The conjugated insulin retains its biological activity once released. However, it is not known whether other agents or drugs can be so conjugated or whether such a conjugated form of any drug or other agent would be effective.

The present invention provides a controlled drug delivery system for the controlled release of an unconjugated drug or other agent.

According to the present invention there is provided a method for producing a drug system for delivering a drug for the treatment of a condition, comprising immobilising a drug or other agent in a bio-compatible matrix containing at least one receptor for a physiological substance which will be in the environment of the matrix when administered, said receptor being activated in response to the levels of said physiological substance to effect a conformational change in the matrix allowing mobilisation and release of the drug into the environment.

The agent may comprise a naturally occurring biological agent, for example, a hormone, which may, of course, be insulin, as in U.S. Pat. No. 4,348,387, but now in unconjugated form. Because there is now no need for conjugation, other hormones or drugs which it may not be possible to conjugate or which will not work in the system of U.S. Pat. No. 4,348,387 even if they can be conjugated, or which may be physiologically ineffective or less effective or even harmful when conjugated, may be used according to the invention.

The receptor may be a binding macromolecule, for example, a lectin, which may be concanavalin A, a lectin produced from the jack bean.

The receptor may reversibly bind the physiological substance, which may be a carbohydrate, preferably glucose, or a carbohydrate containing glucose moieties, such as dextran.

Insulin, or any other agent or drug, may be immobilised in the matrix when terminal glucose molecules on dextran bind to concanavalin A to form a gel.

The conformational change in the matrix may be brought about by the displacement of terminal dextran-glucose molecules from the receptor by free glucose in the physiological environment which may of course be blood or other tissue fluid.

The conformational change may be an ungelling of the matrix allowing mobilisation and release of the insulin or other agent or drug.

The invention will be further apparent from the following description with reference to the several figures of the accompanying drawings, which show, by way of example only, one form of the system embodying same.

Figure 1:
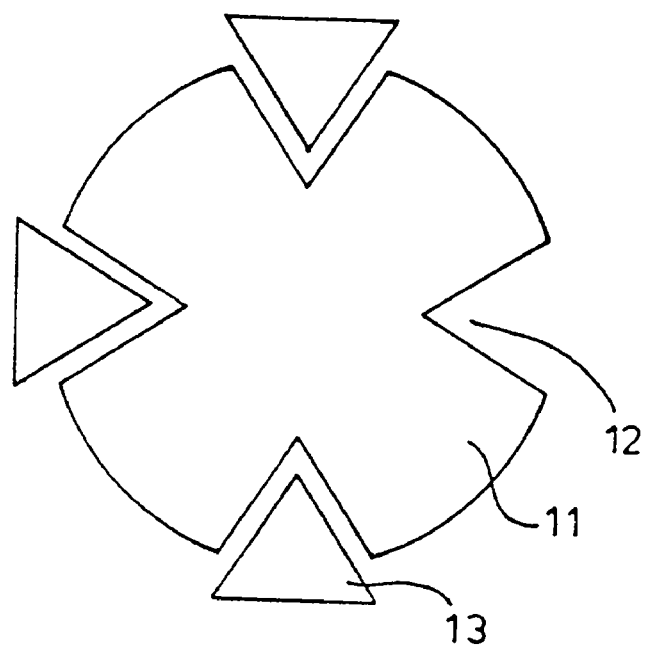
FIG. 1 shows a diagrammatical representation of a concanavalin-A molecule binding glucose.

Referring now to the drawings, it will be seen that the drug delivery system is based on a concanavalin-A molecule 11. Each concanavalin-A molecule 11 has four binding sites 12 specific for sugars, with a high affinity for glucose 13 (FIG. 1). The binding of glucose 13 to the binding site 12 is, however, reversible.

Figure 2:
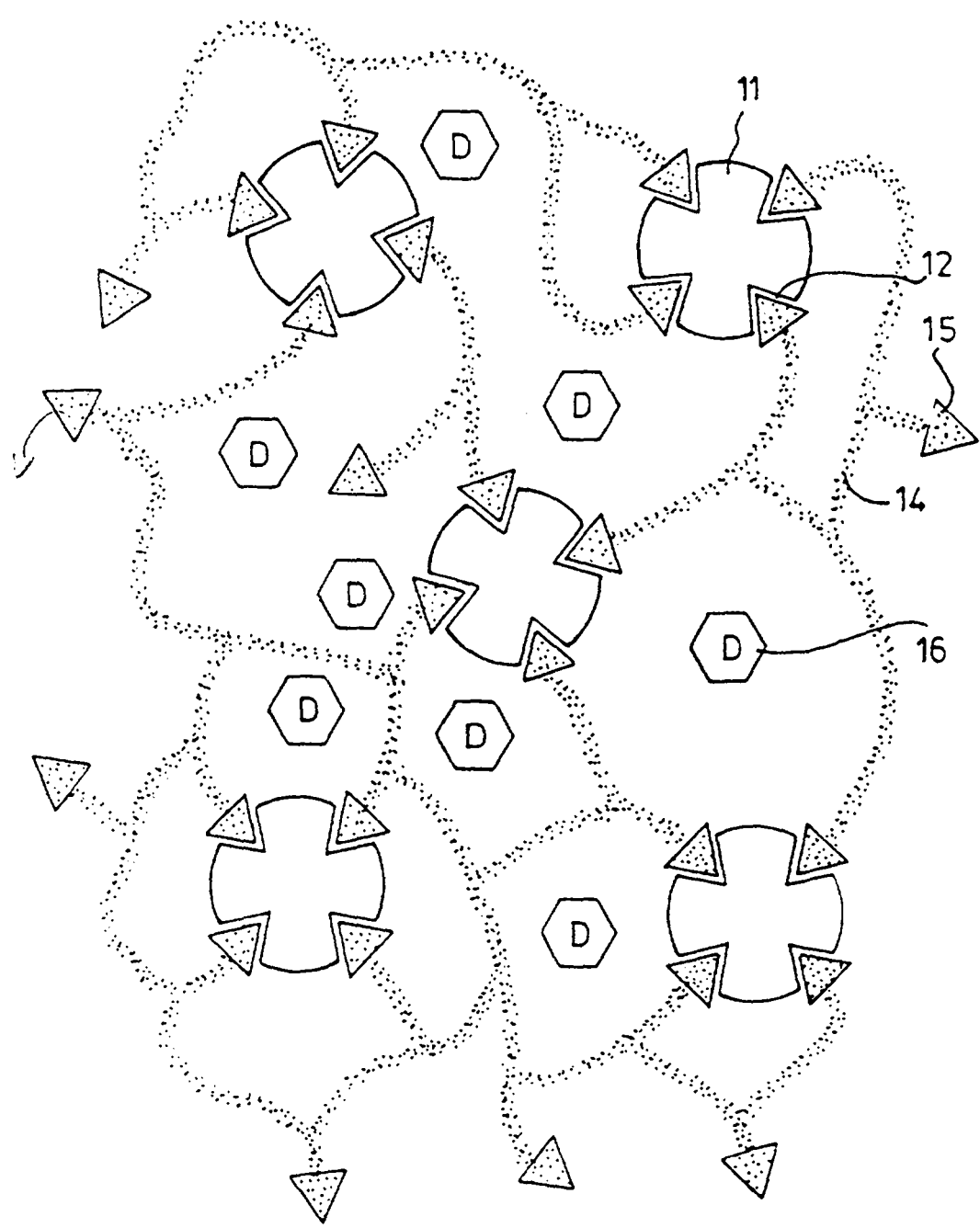
FIG. 2 shows a diagramatical representation of the delivery system, in an inactive form.

The inactive form of the drug system comprises (FIG. 2) glucose present as terminal glucose moieties 15 of the carbohydrate dextran. Dextran is a branched chain polysaccharide with many terminal glucose moieties which can bind to the binding sites 12 of concanavalin-A molecules 11 and in so doing cross-link the concanavalin-A molecules together to form a viscous gel matrix. Insulin 16 is premixed with dextran gel, so that when concanavalin-A is added to the mixture, a gel is formed between the dextran and the concanavalin-A with the insulin relatively immobilised inside the gel matrix unable to escape rapidly (FIG. 2).

Figure 3:
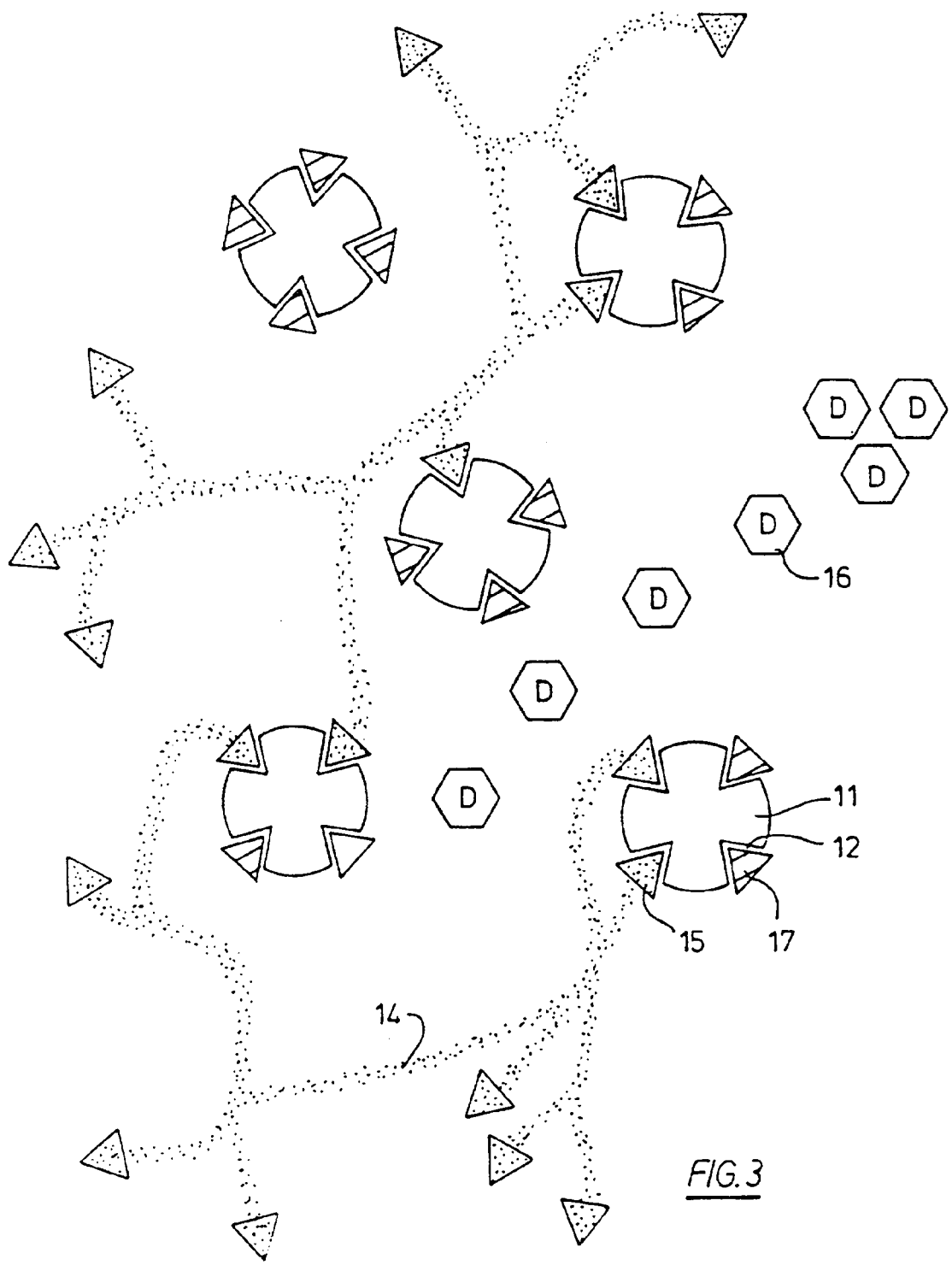
FIG. 3 shows a diagramatical representation of the delivery system, in an active form.

The binding of dextran to concanavalin-A is reversed (FIG. 3) when there is an increase in the concentration of free glucose 17 in the physiological environment. The free glucose displaces the terminal dextran-glucose 15 from the binding sites of the concanavalin A molecules. The matrix undergoes a conformational change allowing mobilisation and release of the insulin into the environment.

Once the level of free glucose falls, in response to the action of the released insulin, the displaced terminal dextran-glucose molecules will re-bind to the concanavalin-A molecules and the matrix will re-gel, thus again restricting insulin remaining in the matrix.

The mechanism of this drug system is thus repeatable and releases insulin in response to a number of free glucose insults, in a similar manner to the in vivo feedback mechanism of the pancreatic cells.

Experiments carried out in vitro show release of a drug, nitrofurantoin, from the drug system in response to a glucose load. The drug nitrofuantoin was chosen to exemplify the invention mainly because it has similar physicochemical properties to some oral hypoglyceamic drugs but is easier to assay. In these experiments the drug system comprised a mixture of the following:

| | |
|---|---|
| Dextran (from Sephadex G-25, fine beads) | 99 mg |
| Drug (Nitrofurantoin) | 39 mg |
| Concanavalin-A preparation comprising | |
| sodium chloride | 15 mg |
| lectin | 3 mg |
| Ethocel 50 cp (water dispersible) | 153 mg |
| TOTAL | 300 mg |

The drug system above was separately tested in both sucrose containing and plain media. The sugar was present at 2% w/v. The pH was 6.2 and the media contained trace quantities of manganese and calcium, important for glucose moiety binding to lectin.

Dextran (uncross-linked AW 2-40×10$^6$ daltons) may be used in place of sephadex G-25 fine beads.

Figure 5:
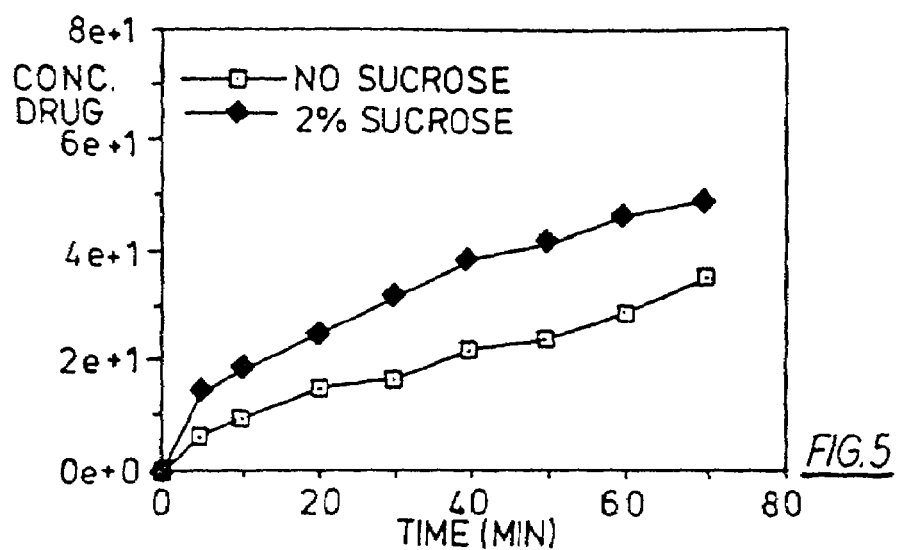
FIGS. 5 to 7 show in vitro experimental results of the drug system.
Figure 6:
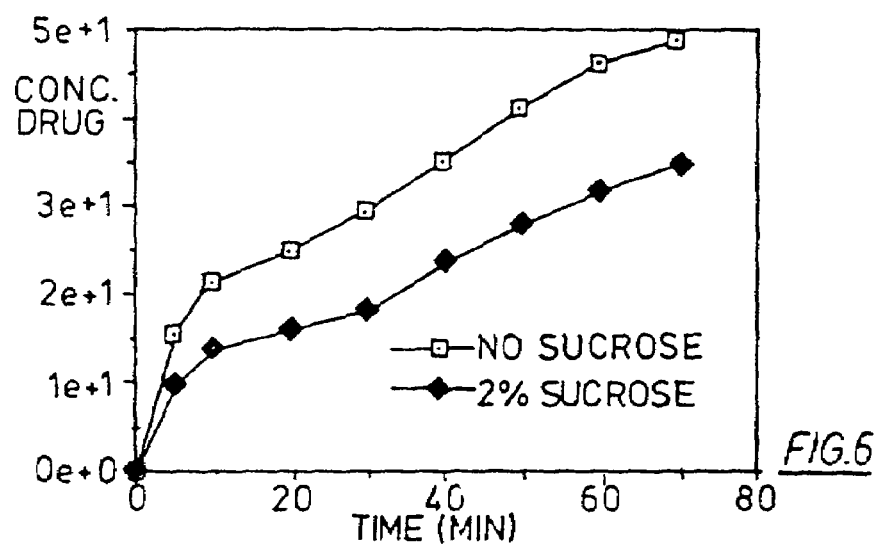
Figure 7:
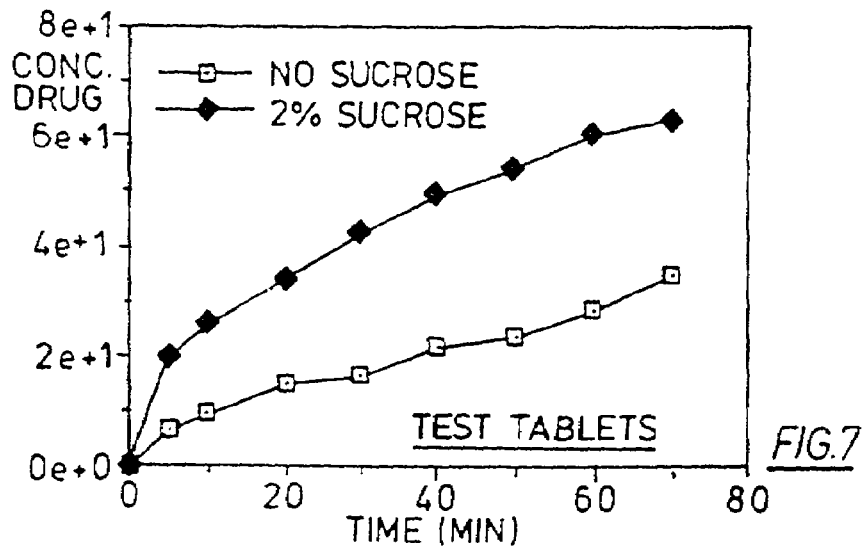

The results are shown in FIG. 5. As can be seen from the graph, the drug was released more quickly from the lectin in the presence of sucrose. A further control experiment was carried out in which the drug system was mixed without any lectin. The results are shown in FIG. 6. A reproducible depression of drug release was seen in the presence of sucrose, probably due to to the viscosity of the diffusion boundary layers. When a correction was made for this effect in the experiment of FIG. 5, the increased rate of release of the drug was even more pronounced (FIG. 7).

The system could be implanted inside a diabetic patient with up to several months supply of insulin. However, since concanavalin-A is itself toxic, it would be desirable to enclose the matrix in a non-erodible material which allows the diffusion of free glucose and insulin into and out of the matrix, but does not allow the escape of the concanavalin-A molecules.

Figure 4:
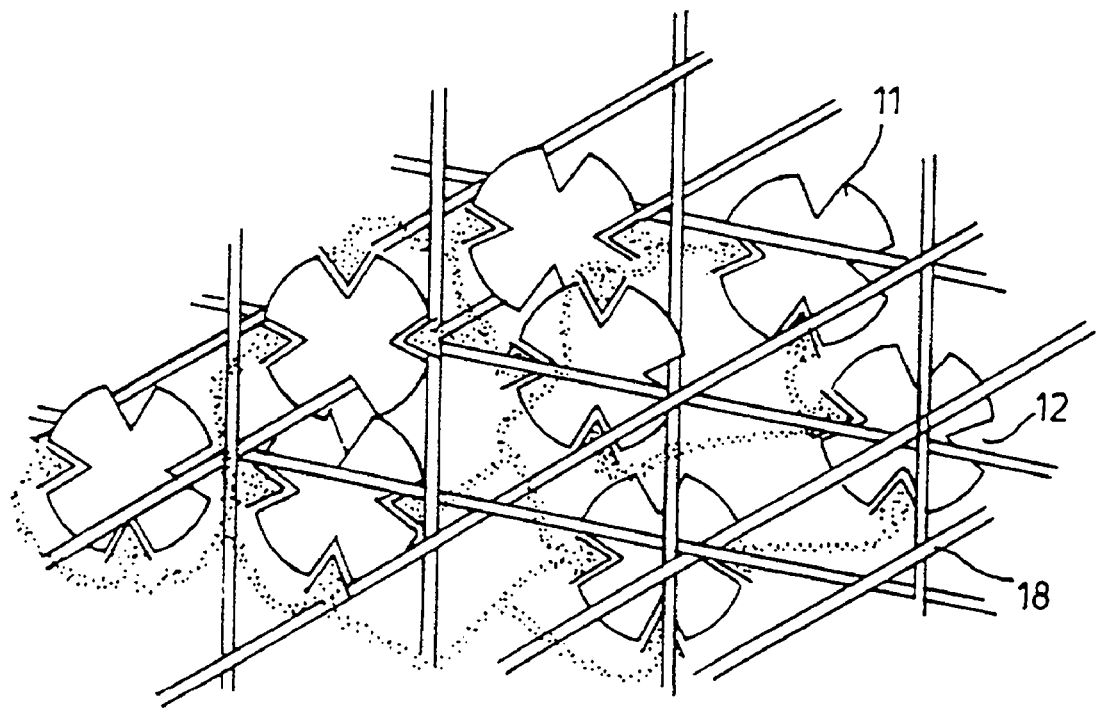
FIG. 4 shows the drug system of FIG. 2 enclosed in a bio-compatible lattice.

An example of such a material is an acrylic permanent gel, covalently cross-linked in situ to form a three dimensional grid structure 18 (FIG. 4). In addition to preventing the escape of toxic concanavalin-A into the bloodstream of a patient, it also allows an implant to be recoverable and possibly 'recharged' with insulin and reused. The acrylic network will also help to prevent overload of the receptor by a high level of irrelevent sugar with subsequent loss of specificity as well as preventing dose-dumping. In such a matrix, restriction of drug diffusion may occur by either an increase in viscosity or precipitation via the dextran-lectin reaction.

Alternatively, the dextran perimeter may be cross-linked with a specific agent, for example, epichlorohydrin to form a membrane of cross-linked dextran around the gel.

It will be appreciated that it is not intended to limit the invention to the above example only, many variations, such as might readily occur to one skilled in the art, being possible, without departing from the scope thereof.

For example, when adminstering anything other than insulin or a drug which is intended to control blood sugar, the drug or agent may be released not by a feed-back mechanism but by a controlled administration of sugar, bringing literally to life the notion of a spoonful of sugar making the medicine go down.

The receptor may be any molecule, natural or engineered, having binding sites for complex branched substrates which would form a gel on binding, but would be displaceable by the 'free' substrate which may be naturally or artificially induced to effect release of a drug or other agent. Lectins other than concanavalin-A, which may be non-toxic or less toxic, may be used, for example, the pea (*Pisium sativum*) lectin.

The invention claimed is:

1. A method of producing a system for delivering a drug or other biological agents, comprising the step of combining a reversible gelled matrix and the drug or other biological agents, wherein the reversible gelled matrix comprises a crosslinking agent and at least one receptor having a plurality of binding sites for a substrate in the environment of the matrix and for the crosslinking agent, the at least one receptor being activated in response to the levels of the substrate to effect a conformational change in the matrix allowing mobilisation and release of the drug or other biological agents into the environment, the conformational change in the matrix allowing mobilisation being effected by the binding of the substrate to the binding sites such that it displaces the crosslinking agent from the binding sites, and the conformational change in the matrix allowing immobilisation being effected by the binding of the crosslinking agent to the binding sites such that when the crosslinking agent becomes bound to the binding sites it displaces the substrate from the binding sites.

2. A method according to claim 1, wherein the drug comprises a naturally occurring biological agent.

3. A method according to claim 2, wherein the biological agent is a hormone.

4. A method according to claim 3, wherein the hormone is insulin.

5. A method according to claim 1, wherein the receptor is a binding macromolecule.

6. The method according to claim 1, wherein the at least one receptor is a lectin.

7. A method according to claim 6, wherein the lectin is concanavalin A, a jack bean lectin.

8. A method according to claim 6, wherein the lectin is a pea lectin.

9. The method according to claim 1, wherein the at least one receptor is synthetic.

10. A method according to claim 1, wherein the substrate is a physiological substance.

11. A method according to claim 10, wherein the physiological substance is a carbohydrate.

12. A method according to claim 11, wherein the carbohydrate is glucose.

13. The method according to claim 12, wherein the crosslinking agent is dextran, terminal glucose moieties on the dextran binding to the at least one receptor.

14. The method according to claim 1, wherein the drug is immobilised in the gelled matrix when terminal glucose moieties on dextran bind to concanavalin A.

15. The method according to claim 1, wherein the conformational change in the matrix allowing mobilisation is an ungelling and the conformational change in the matrix allowing immobilisation is a gelling.

16. The method according to claim 1, wherein the system delivers a drug or other biological agents for the treatment of a condition.

17. A system for delivering a drug or other biological agents, comprising a reversible gelled matrix containing an immobilised drug or other biological agents, wherein the reversible gelled matrix comprises a crosslinking agent and at least one receptor having a plurality of binding sites for a substrate in the environment of the matrix and for the crosslinking agent, the at least one receptor being activated in response to the levels of the substrate to effect a conformational change in the matrix allowing mobilisation and release of the drug or other biological agents into the environment, the conformational change in the matrix allowing mobilisation being effected by the binding of the substrate to the binding sites such that it displaces the crosslinking agent from the binding sites, and the conformational change in the matrix allowing immobilisation being effected by the binding of the crosslinking agent to the binding sites such that when the crosslinking agent becomes bound to the binding sites it displaces the substrate from the binding sites.

18. The system according to claim 17, wherein the conformational change in the matrix allowing mobilisation is an ungelling and the conformational change in the matrix allowing immobilisation is a gelling.

19. The system according to claim 17, wherein the system delivers a drug or other biological agents for the treatment of a condition.

20. Te method of claim 1, wherein the at least one receptor does not have a binding site for the drug or biological agents.

21. The method of claim 17, wherein the at least one receptor does not have a binding site for the drug or biological agents.

22. A method of producing a system for delivering a drug or other biological agents, comprising the step of combining:
a drug or other biological agents;
at least one polyfunctional branched polysaccharide crosslinking agent; and
at least one polyfunctional receptor,
wherein the at least one crosslinking agent and the at least one receptor form a reversible gelled matrix and the at least one receptor has a plurality of binding sites for a substrate in the environment of the matrix and for the crosslinking agent.

23. The method according to claim 22, wherein the at least one receptor is activated in response to the levels of the substrate to effect a conformational change in the matrix allowing mobilisation and release of the drug or other biological agents into the environment, a conformational change in the matrix allowing mobilisation is effected by the binding of the substrate to the binding sites such that it displaces the crosslinking agent from the binding sites, and the conformational change in the matrix allowing immobilisation is effected by the binding of the crosslinking agent to the binding sites such that when the crosslinking agent becomes bound to the binding sites it displaces the substrate from the binding sites.

24. The method according to claim 22, wherein the at least one polyfunctional crosslinking agent is dextran.

25. The method according to claim 22, wherein the substrate is a physiological substance.

26. The method according to claim 25, wherein the physiological substance is a carbohydrate.

27. A method of producing a system for delivering a drug or other biological agents, comprising the step of combining a reversible gelled matrix and the drug or other biological agents, wherein the reversible gelled matrix comprises a crosslinking agent and at least one receptor having a plurality of binding sites for a substrate in the environment of the matrix and for the crosslinking agent while not having binding sites for the drug or other biological agents, the at least one receptor being activated in response to the levels of the substrate to effect a conformational change in the matrix allowing mobilisation and release of the drug or other biological agents into the environment, the conformational change in the matrix allowing mobilisation being effected by the binding of the substrate to the binding sites such that it displaces the crosslinking agent from the binding sites, and the conformational change in the matrix allowing immobilisation being effected by the binding of the crosslinking agent to the binding sites such that when the crosslinking agent becomes bound to the binding sites it displaces the substrate from the binding sites.

28. A system for delivering a drug or other biological agents, comprising a reversible gelled matrix containing an immobilised drug or other biological agents, wherein the reversible gelled matrix comprises a crosslinking agent and at least one receptor having a plurality of binding sites for a substrate in the environment of the matrix and for the crosslinking agent while not having binding sites for the drug or other biological agents, the at least one receptor being activated in response to the levels of the substrate to effect a conformational change in the matrix allowing mobilisation and release of the drug or other biological agents into the environment, the conformational change in the matrix allowing mobilisation being effected by the binding of the substrate to the binding sites such that it displaces the crosslinking agent from the binding sites, and the conformational change in the matrix allowing immobilisation being effected by the binding of the crosslinking agent to the binding sites such that when the crosslinking agent becomes bound to the binding sites it displaces the substrate from the binding sites.

29. The system according to claim 28, wherein the conformational change in the matrix allowing mobilisation is an ungelling and the conformational change in the matrix allowing immobilisation is a gelling.

30. A method of producing a system for delivering a drug or other biological agents, comprising the step of combining:
a drug or other biological agents;
at least one polyfunctional branched polysaccharide crosslinking agent; and
at least one polyfunctional receptor,
wherein the at least one crosslinking agent and the at least one receptor form a reversible gelled matrix and the at least one receptor has a plurality of binding sites for a substrate in the environment of the matrix and for the crosslinking agent while not having binding sites for the drug or biological agents.

31. The method according to claim 30, wherein the at least one receptor is activated in response to the levels of the substrate to effect a conformational change in the matrix allowing mobilisation and release of the drug or other biological agents into the environment, a conformational change in the matrix allowing mobilisation is effected by the binding of the substrate to the binding sites such that it displaces the crosslinking agent from the binding sites, and the conformational change in the matrix allowing immobilisation is effected by the binding of the crosslinking agent to the binding sites such that when the crosslinking agent becomes bound to the binding sites it displaces the substrate from the binding sites.

32. A method of producing a system for delivering a drug or other biological agents, comprising the step of combining a reversible gelled matrix and the drug or other biological agents, wherein the reversible gelled matrix comprises a branched polysaccharide crosslinking agent and at least one lectin receptor having a plurality of binding sites for a substrate in the environment of the matrix and for the crosslinking agent, the at least one receptor being activated in response to the levels of the substrate to effect a conformational change in the matrix allowing mobilisation and release of the drug or other biological agents into the environment the conformational change in the matrix allowing mobilisation being effected by the binding of the substrate to the binding site such that it displaces the crosslinking agent from the binding sites, and the conformational change in the matrix allowing immobilisation being effected by the binding of the crosslinking agent to the binding sites such that when the crosslinking agent becomes bound to the binding sites it displaces the substrate from the binding sites.

33. The method of claim 1 wherein the drug or biological agents immobilised in the matrix is unconjugated.

34. The method of claim 17 wherein the drug or biological agents immobilised in the matrix is unconjugated.

35. The method of claim 22 wherein the drug or biological agents immobilised in the matrix is unconjugated.

36. The method of claim 27 wherein the drug or biological agents immobilised in the matrix is unconjugated.

37. The method of claim 28 wherein the drug or biological agents immobilised in the matrix is unconjugated.

38. The method of claim 30 wherein the drug or biological agents immobilised in the matrix is unconjugated.

39. The method of claim 32 wherein the drug or biological agents immobilised in the matrix is unconjugated.

* * * * *